United States Patent [19]

Osburn et al.

[11] Patent Number: 4,534,768
[45] Date of Patent: Aug. 13, 1985

[54] SEALANT PAD FOR EXTERNAL CATHETER AND METHOD OF USE THEREOF

[75] Inventors: Frank G. Osburn, Hanover Park; Kenneth E. Riedel, Naperville, both of Ill.

[73] Assignee: Hollister Incorporated, Libertyville, Ill.

[21] Appl. No.: 397,183

[22] Filed: Jul. 12, 1982

[51] Int. Cl.³ .............................................. A61F 5/44
[52] U.S. Cl. ..................... 604/350; 664/352; 664/355; 128/157; 128/760
[58] Field of Search .................. 604/346–347, 604/349–353, 355, 389, 180; 128/DIG. 26, 157, 158, 153–155, 149, 132, 138 R, 169, 171, 760, 767; 206/447

[56] References Cited

U.S. PATENT DOCUMENTS

| 2,538,136 | 1/1951 | Twachtman | 128/157 |
|---|---|---|---|
| 2,797,687 | 7/1957 | Crawford | 128/157 |
| 2,891,546 | 6/1959 | Galloway | 128/295 |
| 2,940,450 | 6/1960 | Witt | 128/295 |
| 2,976,869 | 3/1961 | Silverstone | 128/295 |
| 2,977,267 | 3/1961 | Douthitt | 206/447 |
| 3,339,551 | 9/1967 | Stoutenburgh | 128/295 |
| 3,340,876 | 9/1967 | Hill | 604/347 |
| 3,364,932 | 1/1968 | Beach | 128/295 |
| 3,421,504 | 1/1969 | Gibbons | 128/295 |
| 3,511,241 | 5/1970 | Lee | 128/295 |
| 3,526,227 | 9/1970 | Appelbaum | 128/295 |
| 3,631,857 | 1/1972 | Maddison | 128/295 |
| 3,644,252 | 2/1972 | Shenfeld et al. | 260/27 R |
| 3,721,243 | 3/1973 | Hesterman | 128/295 |
| 3,742,953 | 7/1973 | Lee | 128/295 |
| 3,788,324 | 1/1974 | Lim | 128/295 |
| 3,835,857 | 9/1974 | Rogers | 128/295 |
| 3,863,638 | 2/1975 | Rogers | 128/295 |
| 4,187,851 | 2/1980 | Hauser | 128/157 |
| 4,254,008 | 3/1981 | Krsek | 604/336 |
| 4,284,079 | 8/1981 | Adair | 128/760 |
| 4,346,525 | 8/1982 | Larsen et al. | 128/586 |
| 4,348,502 | 9/1982 | Coran et al. | 525/183 |
| 4,378,018 | 3/1983 | Alexander et al. | 128/760 |

FOREIGN PATENT DOCUMENTS

| 162302 | 2/1958 | Sweden | 128/157 |
|---|---|---|---|
| 4175 | 9/1893 | United Kingdom | 128/154 |
| 960864 | 6/1964 | United Kingdom | 128/157 |

Primary Examiner—Richard J. Apley
Assistant Examiner—Greg Beaucage
Attorney, Agent, or Firm—Tilton, Fallon, Lungmus

[57] ABSTRACT

An improved sealant pad for sealing and retaining in place the elastic sheath of a male urinary drainage catheter. The adhesive sealant pad, in addition to being soft, pliable, stretchable, and urine-resistant, is planar (when undeformed), has a distinctive cloverleaf outline, is composed of a material with elastic recovery, and has an oval-shaped opening which, in preparation for application of the pad to a patient, is reformed into generally circular shape.

26 Claims, 8 Drawing Figures

SEALANT PAD FOR EXTERNAL CATHETER AND METHOD OF USE THEREOF

BACKGROUND

Co-pending co-owned application Ser. No. 271,082, filed June 5, 1981, now U.S. Pat. No. 4,378,018, discloses a male urinary drainage device that takes the form of an elastic sheath and a resilient, deformable sealant pad. The pad has a central ring portion adapted to extend about the penis, preferably directly behind the glans thereof, and at least one radial strap portion designed to extend along the penile shaft. In a preferred embodiment, two such strap portions project from diametrically opposite sides of the central ring portion. The entire pad is formed of a resilient, compressible, deformable, water-resistant material, and opposite sides of the pad are sufficiently tacky to provide an effective and retentive seal between the pad and the penis, and between the pad and the overlying sheath. Specifically, the central ring portion of the pad sealingly engages both the penis and the sheath to provide an effective barrier against fluid backup, whereas the strap portions perform a primary function in maintaining the sheath and pad in place. Release strips or sheets on one or both sides of the pad facilitate handling of the pad and proper placement of the pad upon a wearer.

Various other devices have been disclosed in the prior art for use by male patients afflicted with urinary incontinence as a result of injury, disease, advanced age, or any other cause. U.S. Pat. No. 2,940,450 discloses a drainage device in the form of a penile sheath connected to a flexible tube leading to a suitable receptacle, the sheath being held in place by drawstrings which may be tied together to produce a secure fit. In U.S. Pat. No. 3,835,857, elastic adhesive tape is wrapped about the sheath in place of drawstrings, and in U.S. Pat. No. 3,863,638 a liner is disposed beneath the sheet to reduce leakage and promote patient comfort. U.S. Pat. No. 4,187,851 discloses a method of forming such a liner in place by wrapping the penile shaft with a double-faced adhesive strip prior to application of the elastic sheath. Other patents reflecting the state of the art are U.S. Pat. Nos. 3,421,504, 3,526,227, 2,976,869, 3,339,551, 3,364,923, 3,721,243, 3,631,857, 3,788,324, 3,511,241, 3,742,953, and 2,891,546.

SUMMARY

This invention is concerned with an improvement over the sealant pad disclosed in the aforementioned co-pending application now U.S. Pat. No. 4,378,018. It has been discovered that if such a pad is provided with an oval opening rather than a circular opening, with the oval being oriented so that its short axis is parallel with a pair of wing portions projecting radially outwardly from opposite sides of the central ring portion of the pad, and if the entire pad has a generally cloverleaf-shaped outline, such a pad may be stretched and applied more easily and effectively. Specifically, such a construction allows the ring portion to be more readily reformed from its original flat condition into a generally cylindrical condition for sealing engagement with the penile shaft and the sheath of the external catheter fitted upon the wearer.

The cloverleaf outline is a development of the configuration of the annular central portion of the pad and the manner in which it is integrated with a pair of radially outwardly projecting wing portions. If the pad were viewed with the wing portions omitted, the remaining central portion would be generally oval shaped with the outer perimeter of the flat oval ring being concentric with the oval-shaped opening therein. More precisely, the oval opening is generally elliptical in shape with a width:length ratio, measured along the minor and major axes, within a general range of 0.35:1 to 0.65:1, or within a preferred range of 0.45:1 to 0.60:1. The wing portions are coplanar with the flat elliptical ring portion and project outwardly in opposite directions from the ring portion along the short axis of the ellipse. The edges of the ring portion and the wing portions blend smoothly along curved lines to provide the pad with a distinctive symmetrical cloverleaf outline.

In addition to its other properties, the pliable and stretchable adhesive pad has an elastic recovery so that it may be readily deformed and molded by the fingers but will tend to revert to its original shape when release. Various materials may be suitable for such purpose, as indicated in the aforementioned co-pending application, but a particularly effective material has been found to consist of a mixture of a copolymer resin of ethylene and vinyl acetate (EVA), a hydrophilic acrylamide resin (AA), and a water-insoluble dry tack-providing elastomer, the composition being subjected to ionizing irradiation to form a cross-linked polymer network of the EVA and AA resins.

The oval (elliptical) opening in the unitary pad should have a dimension along its major axis within the general range of about 15 to 30 millimeters (mm) when the pad is unstretched. For any given application, such dimension should approximate, and preferably be slightly less than, the diameter of the penile shaft of the wearer. Therefore, to accommodate wearers of different size, pads having oval openings of different size measured along the major axes thereof may be provided.

A pair of release sheets formed of thin, flexible, and preferably transparent (or highly translucent) and slightly stretchable polymeric film are removably and adhesively secured to opposite surfaces of the flat planar pad, each release sheet having an oval opening in register with the opening of the pad and having a line of separation radiating outwardly therefrom to a point along the outer perimeter of the portion of the sheet overlying the ring portion of the pad.

In use, the pad, covered on opposite faces by the protective release sheets, is gripped by its wing portions and is stretched laterally to reform the oval opening into a circular configuration. At the same time, the wing portions are flexed or deformed into generally parallel relation and the ring portion into a generally cylindrical (or frustoconical configuration. The stretched and deformed pad, with the release sheet still in place, is then fitted over the wearer's penis with the wing portions extending in a proximal direction along opposite sides of the penile shaft and with the generally cylindrical ring portion directly behind the coronal ridge of the glans. The stretching forces are then released, allowed elastic retraction of the pad, the release sheet on the proximal side of the pad is removed, and the pad is pressed and molded into sealing engagement with the penis. Finally, the remaining release sheet is removed and the elastic sheath of the external drainage catheter is fitted over the penis and pressed into sealing engagement with the adhesive sealant pad.

Other features, advantages, and objects of the invention will become apparent from the specification and drawings.

DRAWINGS

DETAILED DESCRIPTION OF PREFERRED EMBODIMENT

Figure 1:
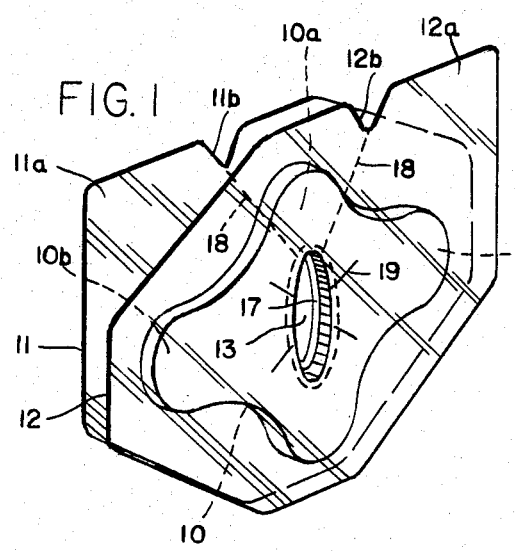
FIG. 1 is a perspective view of a sealant pad embodying the invention, the pad appearing as it would be available to the user protected by a pair of release films covering opposite faces thereof.
Figure 2:
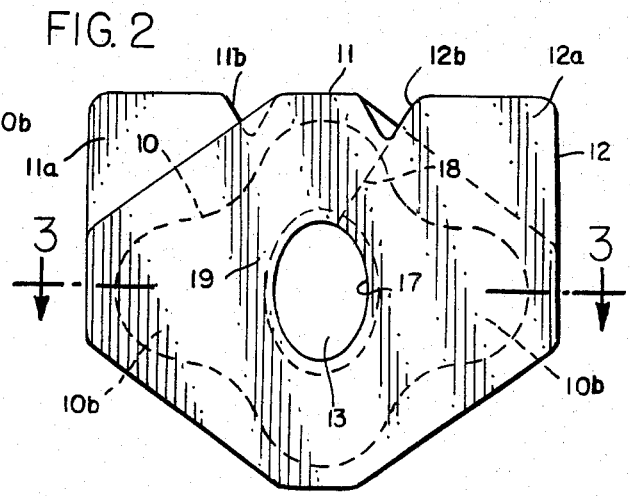
FIG. 2 is a elevational view of the pad with the release sheets in place.
Figure 3:
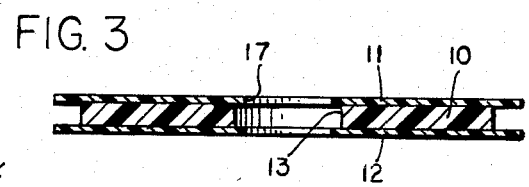
FIG. 3 is a horizontal sectional view taken along line 3—3 of FIG. 2.

Referring to FIGS. 1-3, the numeral 10 generally designates a sealant pad embodying this invention, the pad being shown as it would be supplied to the user with protective release sheets 11 and 12 covering opposite faces of the pad. In its undeformed state, the pad is generally planar with flat opposite faces and has a thickness within the general range of about 1.5 to 3 mm. The pad is formed entirely of a soft, pliable polymeric material having characteristics of stretchability, at least limited elastic recovery, and stability upon exposure to urine. In addition, the opposite faces of the pad should be tacky or have pressure-sensitive adhesive properties achieved either by coating such faces with an appropriate adhesive or by compounding the material of the pad with a material having tackiness as one of its properties. A variety of materials might be used to achieve suitable results, and reference may be had to co-pending application Ser. No. 271,082, filed June 5, 1981, now U.S. Pat. No. 4,378,018, for a discussion of commercially-available materials, and appropriate modifications of such materials, for such purpose. One such material is described in U.S. Pat. No. 2,570,182 as being composed of a blend of nitro rubber and polyvinyl chloride. A material marketed under the name "Ensolite" by Uniroyal, Inc., has been used in sheet form for a male urinary drainage device and is described in U. S. Pat. No. 4,187,851. Another such material is composed primarily of polyisobutylene, such material having been used in ostomy rings and blankets, and having been sold under the name "Crixiline" by Danal Laboratories, Inc., St. Louis, Mo. Other suitable materials can be formulated from gelled mixtures of hydrocolloids such as karaya or sodium carboxymethyl cellulose and polyhydroxy alcohols such as glycerine or propylene glycol, which preferably includes a few percent of fumed silica, as described in co-pending application U.S. Pat. Ser. No. 185,003, filed Sept. 8, 1980. To further improve the desired properties of such compositions for use in the present invention, a minor proportion of polyacrylamide resin can be incorporated, and cross-linked by gamma irradiation. See U.S. Pat. Nos. 4,115,339 and 4,258,715.

A particularly effective material for use in practicing this invention is believed to be the barrier material of co-pending co-owned application U.S. Pat. Ser. No. 397,184, filed July 12, 1982, now abandoned and superceded by U.S. Pat. Ser. No. 550,020, filed Nov. 8, 1983, now U.S. Pat. No. 4,477,325, which takes the form of a cross-linked polymer network with a water-insoluble dry tack-providing elastomer dispersed therethrough. The polymer network utilizes as a principal ingredient the copolymer resin of ethylene and vinyl acetate (EVA), which is employed in combination with a lesser amount of a hydrophilic polyacrylamide (AA), or hydrophilic resin cross-linking with the EVA. Preferably, a homogeneous mixture is prepared of the EVA and AA resins and an elastomer(s) such as polyisobutylene. This mixture, after being formed into the desired shape, is subjected to cross-linking gamma irradiation which forms the polymer network. If desired, a minor amount of a hydrocolloid such as karaya can be incorporated. The resulting cross-linked molded sheet material has a combination of properties particularly important for an effective sealant pad, being soft, flexible, and stretchable, while providing good mechanical strength and excellent elastic recovery when distorted from its original shape. In addition, the fluid endurance (especially with respect to urine) of the formulation is remarkably good, and the composition exhibits minimal swelling while still being adequately water-absorbing and providing satisfactory wet tack.

In general, the EVA resin may contain from 25 to 65% by weight of vinyl acetate, the amount of ethylene present being correspondingly from 75 to 35%. EVA resins containing relatively large amounts of vinyl acetate are preferred, such as EVA resins containing from 40 to 60% by weight of vinyl acetate. Suitable EVA resins are available from a number of commercial sources. For example, "Ultrathene" and "Vynathene" are sold by U.S.I. Chemicals Co., Division of National Distillers & Chemical Corp., New York, N.Y.

The AA resin may be non-ionic or may contain cationic or anionic groups. Anionic carboxylic acid groups may be introduced by copolymerizing acrylamide with sodium acrylate, and cationic groups introduced by copolymerizing an acrylamide with beta-methacryloxyethyltrimethylammonium methyl sulfate. A cationic acrylamide resin sold as "Reten" polymers by Hercules Incorporated, Wilmington, Del., may be used effectively.

Where the composition is to be irradiated to provide the cross-linked network of the EVA and the AA or other hydrophilic polymer, from 0.1 to 0.5 parts by weight of the hydrophilic resin should be used per part of the EVA resin. Preferably the amount of AA or other hydrophilic resin will range from 0.25 to 0.4 parts by weight per part of the EVA resin.

A third principal ingredient for incorporation with the EVA and AA resins is a suitable elastomer, such as the synthetic rubbers which have heretofore been used in skin barrier compositions. Such synthetic rubbers are water-insoluble and provide an adhesive, dry tack characteristic. See U.S. Pat. Nos. 3,339,546 and 4,253,460 for further description of suitable elastomer. Polyisobutylene is a preferred elastomer, but other elastomers or mixtures of elastomers having similar properties may be used. The amount of elastomer may range from as little as 30% by weight of the total composition up to about 65% by weight, with a preferred range being from 40 to 60% of the composition.

A general formula for such an EVA-AA-elastomer composition is as follows:

| General Formula | |
|---|---|
| Ingredients | Parts by Weight |
| EVA copolymer resin | 20 to 50 |
| AA hydrophilic cross-linker resin | 3 to 20 |
| Elastomer | 30 to 65 |

The general formula set out above may be modified by incorporating from 3 to 30 parts by weight of dispersed particles of water-absorbing wet tack-providing hydrocolloid or other water-absorbing particulate substance providing a wet tack characteristic. The hydrocolloid may be a natural vegetable hydrocolloid gum, or mixtures of such gums, such as karaya, gelatin, pectin, guar, etc. Karaya is an especially suitable hydrocolloid for purposes of the present invention, but other hydrocolloids having similar properties can be used.

A preferred formula incorporating the four ingredients is as follows:

| Preferred Formula | |
|---|---|
| Ingredients | Parts by Weight |
| EVA copolymer resin | 25 to 35 |
| AA cross-linker resin | 5 to 15 |
| Polyisobutylene | 40 to 60 |
| Hydrocolloid | 5 to 15 |

Mixtures of the foregoing ingredients may be prepared in a known manner, such as the procedures described in U.S. Pat. Nos. 3,339,546 and 4,253,460. Roll mills, banbury mixers, and similar mixing apparatus may be used to blend the ingredients. Mixing should be continued until a substantially uniform or homogeneous mixture is obtained. The prepared mixture may then be formed into the desired shape by any number of means commonly used for converting plastic and elastomers to such shapes, such means including compression molding and injection molding. Calendering and extrusion of the mixture in sheet form, followed by die cutting into the desired shape may also be used. The latter procedure has manufacturing advantages for producing products from formed sheets.

The formed product made from such ingredients may be used without irradiation; however, improved properties are obtained by subjecting the compositions to cross-linking irradiation. A source of ionizing radiation is used, such as described in U.S. Pat. No. 4,115,339 for cross-linking high molecular weight vinyl polymer. For example, a Cobalt-60 radiation source can be used to provide suitable ionizing gamma irradiation. The level of radiation is not highly critical but is selected to obtain a satisfactory degree of cross-linking without excessive degradation of the elastomer and the hydrocolloid. This can be accomplished within the range of from 0.2 to 8.0 megarads, a preferred range being from about 2 to 4 megarads.

The formed sealant pad 10 has a distinctive outline that may be regarded as a symmetrical cloverleaf outline. A central opening 13 of oval or generally elliptical shape extends through the central portion 10a of the pad. As shown most clearly in FIG. 4, if the outline of the central portion is completed as indicated by broken lines 14, the annular central portion 10a may be viewed as being oval in shape, the remaining portions of the pad constituting a pair of wing portions 10b that project laterally or radially outwardly from the oval ring portion 10a along the minor x axis of the oval opening 13 (and of the oval ring portion 10a). Stated otherwise, the major y axis of the oval opening 13 (and of the oval ring portion 10a) extends midway between the two wing portions 10b and at right angles to the directions of projection of those wing portions.

Figure 4:
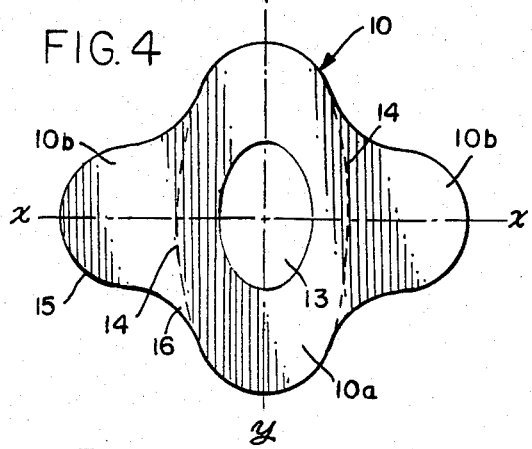
FIG. 4 is an elevational view similar to FIG. 2 but showing the pad with the release sheets removed and illustrating by means of broken lines the relationship between the ring portion and wing portions of the pad.

The paired wing portions 10b have rounded outer edges 15 and, as depicted most clearly in FIG. 4, merge or blend smoothly with the central ring portion 10a along arcuate edges 16. The oval opening 13 is preferably elliptical in shape. In general, the diameter of the opening 13 measured along the major axis y should approximate, or be slightly smaller than, the penile shaft diameter of the intended wearer. It has been found that such an objective may be achieved by providing pads with openings of two different sizes with measurements along the major y axis of about 19 mm and 25 mm, respectively. In any event, the selected dimension of the oval opening, measured along the major axis, for any given pad intended for adult use should fall within the general range of about 15 l to 30 mm. As indicated, the width:length ratio of the oval opening, as measured along the x and y axes, may be varied, but in general it should fall within the range of 0.35:1 to 0.65:1, a preferred range being about 0.45:1 to 0.60:1.

The release films or sheets 11, 12 are each substantially larger in outline than the pad 10 and have oval openings 17 in register with opening 13 of the pad. Each of the openings 17 is of the same shape as opening 13 but is preferably slightly smaller than the pad opening (FIGS. 2, 3) so that the adhesive material of the pad about opening 13 will be protected against contact with other surfaces prior to use.

Each release sheet also includes an upwardly extending tab portion 11a and 12a, respectively, and the sheets are reversed in position so that each of the tabs is fully exposed and may be easily gripped when removal of the release sheets is desired. Adjacent each tab is a notch 11b and 12b, respectively, and a line of separation 18 extends radially inwardly from each such notch to the edge of opening 17 of each release sheet 11, 12. The line of separation may be in the form of a complete line of separation or, as shown, may be an incomplete or perforated line. In any event, a user, by pulling on the tabs 11a and 12a of the release sheets 11 and 12, respectively, may cause separation along lines 18 and thereby facilitate removal of the release sheets from the adhesive pad 10. In addition, the lines of separation 18 may allow limited separation and expansion of each release sheet when the pad is deformed or reformed in use with the release sheets in place, as described hereinafter. Similarly, each sheet may be provided with short relief slits 19 radiating outwardly at different points about the perimeter of each opening 17 to permit expansion of the aligned openings in the pad and release sheets when the pad is stretched and fitted upon a wearer.

The release sheets or films may be formed of any suitable transparent or highly translucent polymeric material that is flexible and preferably slightly stretchable. Low density polyethylene (preferably a density of 0.922 to 0.944) having a film thickness of 2.5 mil has been found particularly effective, but other polymeric film materials having similar properties may be utilized.

Figure 6:
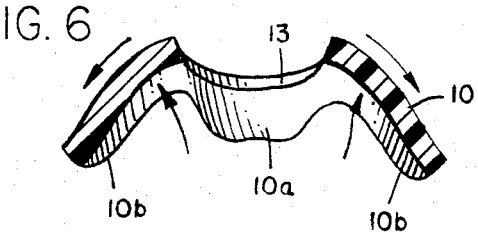
FIG. 6 is a horizontal sectional view taken along line 6—6 of FIG. 5.
Figure 5:
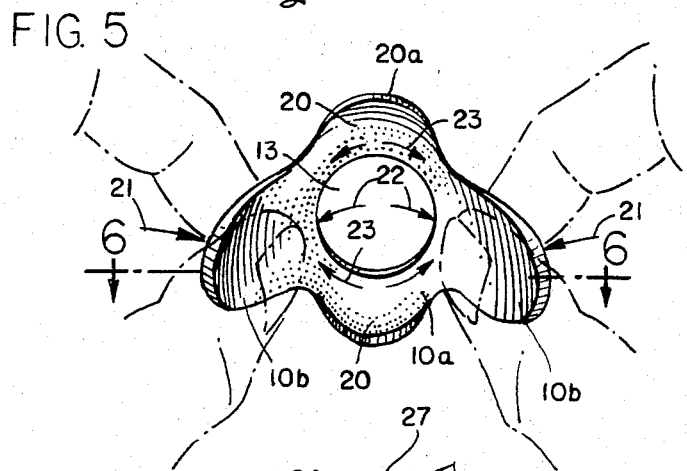
FIG. 5 is a perspective view showing how the pad would be deformed by a user prior to application, the release sheets being omitted only for clarity of illustration.

As an initial step in the use of the pad, wing extensions 10b are gripped between the fingers of each hand and are urged outwardly or laterally to cause a lateral stretching of the upper and lower bridging portions 20 of the central ring 10a of the pad, thereby enlarging opening 13 and causing it to assume a generally circular shape as depicted in FIG. 5. For clarity of illustration, such operation is shown in FIGS. 5 and 6 without the release sheets 11 and 12 in place; however, it is to be understood that during such operation the release sheets are left in contact with opposite sides of the pad. At the same time that such lateral stretching occurs, the wing portions 10b are urged rearwardly or proximally (i.e., towards the patient), out of coplanar relation and into generally parallel relation, as revealed by FIGS. 5 and 6. All of this may be readily accomplished by gripping each of the wing portions between a thumb and index finger (FIG. 5) and simultaneously bending the wing portions 10b towards each other, in the directions of arrows 21, while stretching the ring portion 10a laterally in the directions of arrows 22 to increase the width of bridging portions 20 and to reform opening 13 into generally circular configuration. It is to be noted that the application of such forces causes the tensioned bridging portions 20 to bend rearwardly or proximally in the same general direction as the wing portions because, by so doing, the stretching of the bridging portions along their outer perimeters 20a is kept to a minimum. The primary stretching of those bridging portions occurs in the areas indicated by arrows 23, that is, in the areas along the inner perimeters of the bridging portions along the upper and lower margins of opening 13. The combined results of such stretching and folding action is that the pad, which originally assumed a flat or planar condition, begins to develop a cylindrical configuration and, in addition, the opening 13 of the pad increases in size, particularly in width, so that the pad may be more readily fitted over the glans of the penis.

The release sheets are kept in place during such stretching and folding operations, thereby preventing adherence between the user's fingers and the tacky surfaces of the pad and, in general, facilitating such flexing and stretching manipulations. Circumferential stretching of the inner margin of the pad about opening 13 is not prevented by the release sheets because of the radial slits 19 and the lines of separation 18.

Figure 7:
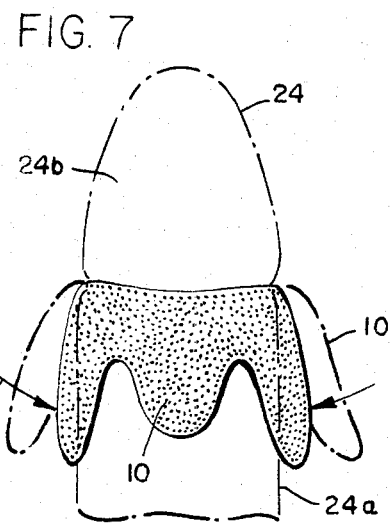
FIG. 7 illustrates a final step of applying the sealant pad to the wearer.
Figure 8:
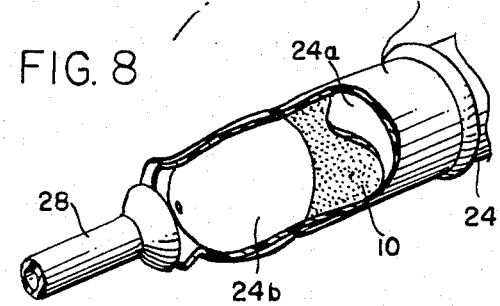
FIG. 8 is a perspective view of the final assembly with the elastic sheath of the external catheter being partially sectioned to reveal the relationship between the sheath and the underlying sealant pad.

When the stretched pad has assumed a condition more cylindrical than planar, it is slipped over the patient's penis 24 to a position directly behind the coronal ridge, the proximal release sheet 12 is removed by pulling tab 12a and causing separation along line 18, and the pad is then allowed to contract into sealing engagement with penile shaft 24a directly behind glans 24b. The deformable pad may be pressed and molded into more complete surface contact with the penis, as indicated by arrows 26 in FIG. 7. Thereafter, the outer release sheet 11 is removed (by pulling tab portion 11a and causing separation of the sheet along line 18), and the elastic sheath 27 of external catheter 28 is fitted over the penis and urged into sealing contact with ring 10 as indicated in FIG. 8.

The external catheter may be of any suitable type, although it is preferred that such catheter be of the construction disclosed in co-pending application Ser. No. 271,082, filed June 5, 1981, as referenced above.

With the catheter in place, the reformed ring portion 10a of the pad, now in generally cylindrical shape, provides a liquid-tight seal against both the penile shaft and the elastic sheath 27, thereby preventing the backflow of urine when the device is in use. The ring portion 10a also helps to retain the sheath in place, but the proximally-directed wing portions 10b, now in generally parallel relation along opposite sides of the penis, perform a major retentive function in not only preventing sliding movement of the sheath with respect to the adhesive pad but also in preventing axial movement of the pad in relation to the penis.

A preferred embodiment of the invention is further illustration by the following example:

EXAMPLE

An adhesive pad having the configuration shown and described herein may be made from a polymer composition prepared in accordance with the following formula:

| Ingredients | Weight % |
|---|---|
| EVA copolymer resin | 31.0 |
| AA resin | 10.0 |
| Polyisobutylene | 48.0 |
| Gum karaya powder | 11.0 |
| | 100.0% |

As set out above, the EVA copolymer resin may contain from 45 to 55% vinyl acetate. For example, the EVA resin may be "Vynathene EY 905" resin (51% vinyl acetate) of U.S. Industrial Chemical Co., Division of National Distillers & Chemical Corp., New York, N.Y. The AA resin may be a cationic acrylamide resin, such as "Reten 210P" resin of Hercules Incorporated, Wilmington, Del. The polyisobutylene may be obtained from Exxon Chemical Co., Elastomer Dept., Houston, Tex., as "Vistanex" Grade LM-MH, or Grade LM-MS, or the "Oppanol" products (B-10 to B-18) of BASF Wyandotte Corp., Holland, Mich. Such polyisobutylenes have a viscosity average molecular weight within the range from about 36,000 to 58,000 (Flory). The gum karaya powder is preferably in finely divided form, such as smaller than about 140 mesh, and containing from about 10 to 18% moisture.

The AA resin and the gum karaya, both being in powder form, are mixed to produce a dry blend. A ribbon blender or other powder mixer can be used for this purpose. Using a kneading-type or comparable mixer, the polyisobutylene is mixed for approximately one minute, the EVA resin is added, and mixing is continued for about 5 minutes. The dry blend is then added incrementally while mixing is continued and until all of the powder has been uniformly dispersed in the other ingredients. The completed homogeneous mixture is then discharged and formed into loaves for further processing. The loaves may be stored on trays until ready for use in forming the molded products.

The foregoing composition and other compositions of this invention may be formed into sheets by passing the material through a calender having a pre-set gap, or the sheets may be formed by compression in a mold cavity of the desired depth. The compositon may also be formed by passing the mixed material through conventional extrusion equipment equipped with a slot or tape die set to extrude a ribbon of approximately the desired thickness. If necessary the extruded ribbon can be further compressed in thickness by passing it through one or more sets of compression rollers. The currently preferred mode of preparation consists of extruding a ribbon of the desired width and thickness directly onto release paper, which is then cut into stock "performs" in the shape shown in FIG. 4. The preforms are then covered, on their exposed sides, with release sheets formed of polyethylene or other suitable film.

While in the foregoing we have disclosed an embodiment of the invention in considerable detail for purposes of illustration, it will be understood by those skilled in the art that many of these details may be varied without departing from the spirit and scope of the invention.

We claim:

1. A sealant pad for a male urinary continence device, comprising a thin planar pad formed entirely of soft, pliable polymeric material having characteristics of stretchability, elastic recovery, surface tackiness, and stability upon exposure to urine; said pad having a flat oval-shaped ring portion with outer limits of generally elliptical shape and a pair of integral coplanar wing portions projecting radially outwardly from diametrically opposite sides of said ring portion beyond said outer limits thereof; said ring portion having an oval opening extending therethrough and oriented with its minor axis aligned in the direction of said wing portions, whereby, when said wing portions are gripped between the fingers of both hands and urged apart, the width of said oval opening increases and those stretches of said oval-shaped ring portion extending between said wing portions tend to flex towards each other.

2. The sealant pad of claim 1 in which said oval opening has a dimension along the major axis thereof falling within the range of about 15 to 30 millimeters when said pad is in an unstretched state.

3. The sealant pad of claim 2 in which said oval opening is in the general shape of an ellipse.

4. The sealant pad of claim 3 in which the width-:length ratio of said opening measured along the minor and major axes thereof when said pad is in an unstretched state falls within the range of 0.35:1 to 0.65:1.

5. The sealant pad of claim 4 in which said ratio falls within the range of 0.45:1 to 0.60:1.

6. The sealant pad of claim 1 in which said pad has a thickness within the range of about 1.5 to 3 millimeters.

7. The sealant pad of claim 1 in which said wing portions and said ring portion have arcuate edges that merge and blend smoothly with each other.

8. The sealant pad of claim 7 in which said wing portions have ends of rounded outline.

9. The sealant pad of claims 1, 2, or 4 in which said polymeric material consists essentially of a cross-linked polymer network with a water-insoluble dry tack-providing elastomer dispersed therethrough, said material being further characterized in that said copolymer network has been formed by cross-linking irradiation of a homogeneous mixture of said elastomer, copolymer of ethylene and vinyl acetate (EVA) resin, and a hydrophilic resin capable of cross linking with the EVA, said EVA resin containing from 25 to 65% by weight of vinyl acetate, and from 0.1 to 0.5 parts by weight of said hydrophilic resin being used per part of said EVA resin.

10. The sealant pad of claim 9 in which said EVA resin contains from 40 to 60% by weight of vinyl acetate.

11. The sealant pad of claim 9 in which said hydrophilic resin is an acrylamide (AA) resin, and from 0.25 to 0.4 parts by weight of said AA resin are used per part of said EVA resin.

12. A sealant pad combination for a male urinary incontinence device, comprising a thin planar pad having flat opposite surfaces and formed entirely of soft, pliable polymeric material having characteristics of stretchability, elastic recovery, surface tackiness, and stability upon exposure to urine; said pad having a flat oval-shaped ring portion with outer limits of generally elliptical shape and a pair of integral coplanar wing portions projecting radially outwardly from diametrically opposite sides of said ring portion beyond said outer limits thereof; said ring portion having an oval opening extending therethrough and oriented with its minor axis aligned in the direction of said wing portions; and a pair of thin, flexible release sheets covering said opposite surfaces of said pad; each of said release sheets having an outline substantially larger than said pad and being provided with an oval aperture in register with the opening in said pad; each release sheet having a line of separation extending from the perimeter thereof to a point along the edge of said aperture adjacent the intersection of said major axis with said edge, whereby, when said wing portions, covered by said release sheets, are gripped between the fingers of both hands and urged apart, the width of said oval opening of said pad and said oval apertures of said sheets increase in size and those stretches of said ring portion extending between said wing portions tend to flex towards each other.

13. The combination of claim 12 in which each of said release sheets is slightly stretchable.

14. The combination of claim 12 in which each of said release sheets is substantially transparent.

15. The combination of claim 12 in which each of said release sheets has a plurality of circumferentially-spaced relief slits projecting radially outwardly from the edge of said aperture.

16. The combination of claim 12 in which each of said release sheets has an outwardly-projecting tab portion, the tab portions of the respective release sheets being offset with respect to each other.

17. The combination of claim 12 in which said line of separation of each release sheet constitutes a line of perforation.

18. The combination of claim 12 in which said oval opening of said sealant pad has a dimension along the major axis thereof falling within the range of about 15 to 30 millimeters when said pad is in an unstretched state.

19. The combination of claim 12 in which said pad has a thickness within the range of about 1.5 to 3 millimeters.

20. The combination of claims 12, 13, 14, or 18 in which oval openings of said sealant pad is in the general shape of an ellipse.

21. The combination of claim 20 in which the width-:length ratio of said opening measured along the minor and major axes thereof when said pad is in an unstretched state falls within the range of 0.35:1 to 0.65:1.

22. The combination of claim 21 in which said ratio falls within the range of 0.45:1 to 0.60:1.

23. The combination of claims 12, 13, 14, or 18 in which said polymeric material consists essentially of a cross-linked polymer network with a water-insoluble dry tack-providing elastomer dispersed therethrough, said material being further characterized in that said copolymer network has been formed by cross-linking irradiation of a homogeneous mixture of said elastomer, copolymer of ethylene and vinyl acetate (EVA) resin, and a hydrophilic resin capable of cross linking with the EVA, said EVA resin containing 25 to 65% by weight of vinyl acetate, and from 0.1 to 0.5 parts by weight of said hydrophilic resin being used per part of said EVA resin.

24. The combination of claim 23 in which said EVA resin contains from 40 to 60% by weight of vinyl acetate.

25. The combination of claim 23 in which said hydrophilic resin is an acrylamide (AA) resin, and from 0.25 to 0.4 parts by weight of said AA resin are used per part of said EVA resin.

26. A method of using the sealant pad of claim 1 comprising the steps of gripping said wing portions between the fingers of both hands and urging them apart to reform said oval opening into circular shape and thereby cause said stretches of said ring portion bridging said wing portions to flex towards each other, while simultaneously bending said wing portions in the general direction of flexure of said stretches of said ring portion; inserting the glans of a patient's penis through the reformed circular opening of said pad to position the generally parallel wing portions, and said flexed stretches of said ring portions bridging said wing portions, alongside the penile shaft directly behind the corona of the glans; whereby, upon release of the wing portions, the pad may be readily molded into annular sealing contact with the penis, and an elastic sheath of an external catheter may then be fitted over the penis and the sealant pad secured to it.

* * * * *